United States Patent [19]

Berger

[11] 4,028,466

[45] * June 7, 1977

[54] ANALGESIC COMPOSITIONS COMPRISING DEXTRO-PROPOXYPHENE AND BENZODIAZEPINE AND PROCESS

[76] Inventor: Frank M. Berger, 190 E. 72nd St., New York, N.Y. 10021

[ * ] Notice: The portion of the term of this patent subsequent to Apr. 12, 1994, has been disclaimed.

[22] Filed: Mar. 10, 1976

[21] Appl. No.: 665,595

Related U.S. Application Data

[63] Continuation-in-part of Ser. No. 541,968, Jan. 7, 1975, abandoned, which is a continuation-in-part of Ser. No. 463,350, April 23, 1974, abandoned.

[52] U.S. Cl. .................................. 424/244; 424/311
[51] Int. Cl.² ................... A61K 31/22; A61K 31/33
[58] Field of Search ........................... 424/244, 311

[56] References Cited

UNITED STATES PATENTS 3,845,192  10/1974  Miller ................................ 424/244

OTHER PUBLICATIONS

Current Therapeutic Research, 16 No. 4, pp. 324–337, (1974).
Sternbach, The Journal of Organic Chemistry, 26–1111 (1961).

*Primary Examiner*—Stanley J. Friedman

[57] ABSTRACT

Analgesic compositions having a remarkably high analgesic activity and a process for obtaining an analgesic effect are provided, in which the active components are dextro-propoxyphene and at least one of certain benzodiazepines. The analgesic activity of these combinations is remarkable, inasmuch as the benzodiazepines when administered separately do not display appreciable analgesic activity, and moreover benzodiazepines that are pharmacologically inert may also be effective in these combinations.

18 Claims, No Drawings

ANALGESIC COMPOSITIONS COMPRISING DEXTRO-PROPOXYPHENE AND BENZODIAZEPINE AND PROCESS

This application is a continuation-in-part of Ser. No. 541,968, filed Jan. 7, 1975, which in turn is a continuation-in-part of Ser. No. 463,350, filed Apr. 23, 1974, both now abandoned.

Propoxyphene, 4-dimethylamino-3-methyl-1,2-diphenylpropionooxybutane, is related structurally to methadone, and has the formula

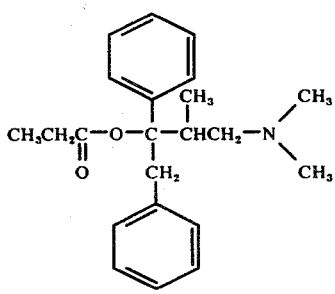

Propoxyphene

The compound exists as four stereoisomers.

The less soluble diastereoisomer is designated as the α-isomer, and the more soluble as the β-isomer. The α,d,l- and α,-d-diastereoisomers have marked analgesic activity. The α,-l-diastereoisomer has no analgesic action, but is has antitussive activity. The β-diastereoisomers are substantially inactive. The United States Dispensatory, 26th Edition, page 963, indicates that the α, dextro isomer, α, d-propoxyphene hydrochloride, is as effective in humans as codiene phosphate in relieving pain. On the other hand, the α,-d,l-racemate has about one-half the analgesic potency of codeine, due no doubt to the presence in an amount of 50% by weight of the analgesically-inactive α, laevo isomer. Regarding the α, laevo isomer, The United States Dispensatory states that, in contrast to propoxyphene, l-propoxyphene has therapeutically useful antitussive activity but no analgesic action.

α,-d-propoxyphene has little, if any, addicting liability, and is used to provide relief in mild to moderate pain, whether acute, chronic, or recurrent. It tends to produce fewer gastrointestinal side effects than codeine, but it is not sufficiently potent to relieve severe pain, and it is of little utility as an antitussive. Several formulations of α, d-propoxyphene hydrochloride are available commercially.

Goodman and Gilman, The Pharmaceutical Basis of Therapeutics, 3rd Edition, indicate that α, d-propoxyphene produces analgesia by acting on the central nervous system. Oral doses of the order of 65 to 100 mg. are about as effective as oral doses of 65 mg. of codeine. Lower doses, 32 mg. for example, are sometimes no more effective than a placebo, however.

Because of its relatively low activity, except at rather high doses, α, d-propoxyphene has been the subject of investigation, with the view of improving its effectiveness.

Miller, U.S. Pat. No. 3,845,192, patented Oct. 29, 1974, reported that the addition of one or both of the tranquilizers chlordiazepoxide and diazepam to α, d-propoxyphene even at doses below those at which these benzodiazepines exhibit tranquilizing effects results in improved analgesia, notably a higher pain threshold. No other benzodiazepines are referred to.

Miller, U.S. Pat. No. 3,749,797, patented July 31, 1973 suggested combinations of α, d-propoxyphene and namoxyrate, and U.S. Pat. No. 3,800,041 suggested combinations of α, d-propoxyphene and indomethacin, each of which give an enhanced analgesic effect.

Certain benzodiazepines have the ability to depress the central nervous system (which can manifest itself as tranquilizing or hypnotic action). L. de Angelis, U. Traversa and R. Vertua in a paper entitled "Structure-activity relationships within the class of 1,4-benzodiazepines: presence of chlorine and central nervous system activities" published in Current Therapeutic Research, 16 No. 4, 324 to 337 (1974) reported that the presence of 7-Cl substituents (as in chlordemethyldiazepam) imparts the highest potency to the molecule. On the other hand, the absence of such a radical (as in dechloro-demethyl diazepam) virtually induces a complete loss of activity. Thus, DDD Azepam is pharmacologically inert. This benzodiazepine has the formula:

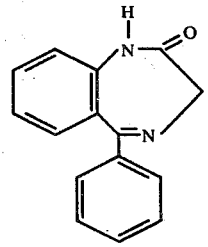

However, the presence of a 7-Cl substituent does not guarantee pharmacological activity. Sternbach, the discoverer of chlordiazepoxide (Librium), diazepam (Valium) and many other benzodiazepines, reported in The Journal of Organic Chemistry 26 1111 (1961) that 2-aminoethylamino-5-phenyl-7-chlorobenzodiazepine-4-oxide, called "Compound 3" for short, is pharmacologically inactive, lacking tranquilizing and hypnotic properties, and is not used medicinally. It has the following structural formula:

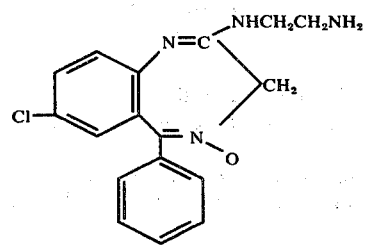

In accordance with the instant invention, it has now been determined that combinations of α, d-propoxyphene with one or more of selected benzodiazepines display an enhanced analgesic activity, greater than that of α, d-propoxyphene or the benzodiazepine alone. That such combinations have an enhanced analgesic activity is quite remarkable, in view of the lack of appreciable analgesic activity of the benzodiazepine component. While it might be expected that combinations containing α, d-propoxyphene would have at least the analgesic activity of α, d-propoxyphene, it would not be expected that combinations containing both the α, d-propoxyphene and benzodiazepine would have an enhanced analgesic activity, inasmuch as the benzodiazepines are not analgesics. Some of the benzodiazepines effective in the combinations of the invention are in fact pharmacologically inert, and are not even tranquilizers.

The benzodiazepines of which at least one and optionally two, three or more can be employed in combinations with α, d-propoxyphene are defined by the formula:

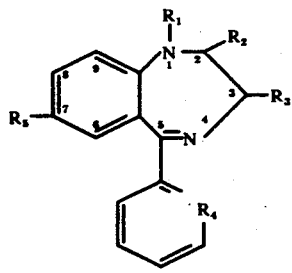

In the above formula, the R substituents are defined as follows:

$R_1$ is selected from the group consisting of hydrogen, n-butyl, and alkylamino of the type

in which R and R' are selected from the group consisting of hydrogen, lower alkyl having from one to three carbon atoms, and bivalent alkylene having from two to four carbon atoms, and linked to the nitrogen at two positions to form a heterocyclic ring;

$R_2$ is selected from the group consisting of oxo oxygen = O and hydroxyl OH;

$R_3$ is selected from the group consisting of hydrogen, hydroxyl OH and carboxyl COOH;

$R_4$ is selected from the group consisting of

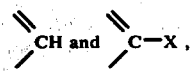

where X is F or Cl; and $R_5$ is selected from the group consisting of H, F and Cl.

Representative benzodiazepines falling within the above formula which can be employed include

| | $R_1$ | $R_2$ | $R_3$ | $R_4$ | $R_5$ |
|---|---|---|---|---|---|
| Oxazepam | H | =O | OH | \>CH | Cl |
| Clorazepate | H | | OH | COOH \>CH | Cl |
| Flurazepam | CH₂—N(CH₂)—N—C₂H₅ / CH₂ \ C₂H₅ | =O | H | \>C—F | Cl |
| Lorazepam | H | =O | OH | \>C—Cl | Cl |
| Prazepam | (CH₂)₂CH₂ | =O | H | \>CH | Cl |

-continued

| | $R_1$ | $R_2$ | $R_3$ | $R_4$ | $R_5$ |
|---|---|---|---|---|---|
| DDD Azepam | H | =O | H | \>CH | H |

The α, d-propoxyphene and benzodiazepine can be employed as the free base or as their pharmaceutically acceptable salts. A pharmaceutically acceptable salt is a salt whose toxicity is not significantly greater than that of the free base. Pharmaceutically acceptable salts are readily prepared by reaction of the free amine with an organic or inorganic acid providing a pharmaceutically acceptable anion. Any pharmaceutically acceptable salt can be used including, for example, the hydrochloride, hydrobromide, sulphate, bisulphate, acetate, salicylate, valerate, oleate, phenate, laurate, borate, benzoate, lactate, phosphate, tosylate, citrate, maleate, fumarate, succinate, tartrate, and napsylate. Usually, the α, d-propoxyphene is employed as the hydrochloride or napsylate salt, and the benzodiazepine is normally employed as the hydrochloride.

In the combinations of the invention, the α, d-propoxyphene gives an effective analgesic effect in a single oral dose providing an amount within the range from about 0.5 to about 30 mg α, d-propoxyphene per kg of animal body weight. The doses can, of course, be varied according to the species of animal being treated, the particular state which is treated, the route of administration, and other factors, as is well known. If the species is a sensitive one, a lesser oral dose will suffice, such as, for a single oral dose, an amount of α, d-propoxyphene within the range from about 0.5 to about 5 mg per kg of animal body weight. In parenteral administration, the doses are lower by a factor of one-third to one-fifth of the amount of the oral doses. For medical applications, it is suggested that reference be made to *The Physician's Desk Reference to Pharmaceutical Specialties and Biologicals*, 27th Edition (1973), Medical Economics, Inc., page 975.

The benzodiazepine is used in an amount to impart enhanced analgesic activity to the analgesic α, d-propoxyphene, which amount accordingly constitutes a potentiating dose. The potentiating dose varies with the benzodiazepine, and also varies with the species of animal, the veterinary or medical state being treated, the route of administration, and other known factors.

Generally, an analgesic effect is obtained by employing any of the benzodiazepines in the normal dosage amounts for the particular diazepine employed when used as a tranquilizer. The tranquilizing dosage amounts for benzodiazepines are set forth in *The Physician's Desk Reference to Pharmaceutical Specialties and Biologicals*, 27th Edition (1973, Medical Economics, Inc., pages 537, 1169, 1178, 1192 and 1567, or in similar publications such as Martindale, *The Extra Pharmacopoeia*, The Pharmaceutical Press, London, 26th Edition (1972). Lesser doses can, however, be used provided only that the relative proportions of benzodiazepine and α, d-propoxyphene in the combinations of the invention are selected to give an analgesic effect. The relative proportions depend, of course, upon the particular benzodiazepine employed, the animal, the veterinary or medical state being treated, the route of administration, and other known factors. In general, however, the weight ratio of α, d-propoxyphene: benzodiazepine is within the range from 100:0.5 to 2:1.

The compositions in accordance with the invention are non-addictive, and consequently administration of the compositions can be repeated intermittently or recurringly, on a regular or irregular basis, as required.

The process in accordance with the invention accordingly comprises administering to a warm-blooded animal both α, d-propoxyphene and a benzodiazepine, separately, i.e., in succession, or together, in amounts to give an enhanced analgesic effect when present together in the animal. In general, the compositions are conveniently administered and accordingly are usually formulated in combination with inert adjuvants appropriate for the particular combination and route of administration that is selected.

The preferred route of administration is orally. The compositions for oral administration can assume any of the normal forms, such as tablets, capsules, suspensions, elixirs, powders and jellies. The compositions can also be administered parenterally, such as by intramuscular, intravenous or subcutaneous administration, using conventional procedures, or in the form of rectal suppositories.

In combinations with adjuvants and inert diluents, the compositions of the invention can have any desired concentration of the active ingredients, i.e., the α, d-propoxyphene and the benzodiazepine. A more concentrated composition can be formulated for dilution with water or other inert liquid before use. Usually, however, it is convenient to have the composition available in unit dose form, i.e., a unit dosage amount such that one portion of the composition provides the normally desired dose. Larger doses can be obtained by combining units, and lesser doses by subdividing units, facilitated by score lines or demarcations of some conventional sort.

The compositions of the invention can also include additional active ingredients to bolster or supplement the analgesic effect, including, for example, aspirin, acetylsalicylic acid, acetylphenetadine, acetylaminophene, codiene, and similar components.

In accord with usual medical practice, the combinations in accordance with the invention can be supplied in unit dose compositions comprising from about 25 to about 200 mg of the α, d-propoxyphene (calculated as the free base) and from about 0.5 to about 25 mg of the benzodiazepine or benzodiazepines (calculated as the free base).

In the following Examples, the compositions in accordance with the invention were evaluated using a standardized "hot plate" test for analgesia as described by Nathan B. Eddy and Dorothy Lineback, *The Journal of Pharmacological and Experimental Therapy* 107 385 (1953). It is generally accepted that this test measures analgesic action and that the results obtained in this test are applicable to all kinds of warm-blooded animals including man. The results of the test can be extrapolated to humans in a relative or qualitative but not in a quantitative manner.

The test is carried out by placing mice onto a hot plate, the temperature of which is maintained between 55° and 55.5° C, and determining the reaction time of the test animal to the sensation of heat, evidenced by lifting the front feet and kicking the hind feet. Normal average reaction time for mice prior to administration of the analgesic composition in accordance with the invention is 9.51 ± 1.02 seconds, with more than 90% of the mice falling within the range from 6 to 13 seconds. The lengthening of the reaction time at a given interval following the administration of a substance is a measure of the analgesic effect. No mouse is left on the hot plate for longer than 30 seconds, since injury might result; failure to react in 30 seconds is thus reported as complete analgesia.

In the standardized test, the reaction time of the mice is noted at 10 minute intervals for 1 hour following administration of the analgesic composition being evaluated. However, in the present Examples, the tabulated data in Table I gives only the results at 30 minutes and at 60 minutes following administration. Administration in each case was intraperitoneally. The test dosage is shown in the Table.

EXAMPLES 1 to 15

A number of combinations were made up composed of α, d-propoxyphene and the benzodiazepine named in Table I. In some cases, a number of dosages were used, while in others, only one dosage was used.

The results of the test were as follows:

TABLE I

| Example No. | Compound | Dose (mg/kg) | Number of Mice | Reaction Time at 30 min. after administration | Reaction Time at 60 min. after administration | Number with Complete Analgesia at 30 min. after administration | Number with Complete Analgesia at 60 min. after administration | Death |
|---|---|---|---|---|---|---|---|---|
| Control A | | Untreated | 32 | 10.7 | 10.5 | 0 | 0 | 0 |
| Control B1 | α,d-propoxyphene (Darvon) | 25 | 32 | 13.6 | 11.0 | 0 | 0 | 0 |
| B2 | | 40 | 56 | 15.2 | 12.5 | 8 | 2 | 0 |
| B3 | | 60 | 16 | 23.6 | 17.7 | 11 | 2 | 6 |
| B4 | | 80 | 16 | — | — | 7 | 3 | 6 |
| Control C1 | Oxazepam (Serax) | 25 | 8 | 10.7 | 10.8 | 0 | 0 | 0 |
| 1 | α,d-propoxyphene (Darvon) / Oxazepam (Serax) | 25 / 25 | 8 | 16.3 | 14.5 | 0 | 0 | 0 |
| Control C2 | Oxazepam (Serax) | 50 | 16 | 16.5 | 18.7 | 1 | 0 | 0 |
| 2 | α,d-propoxyphene (Darvon) / Oxazepam (Serax) | 25 / 50 | 16 | 23.8 | 25.5 | 3 | 5 | 0 |
| 3 | α,d-propoxyphene (Darvon) / Oxazepam (Serax) | 40 / 50 | 16 | 27.9 | 25.4 | 12 | 10 | 0 |
| Control D | Flurazepam (Dalmane) | 50 | 8 | 15.4 | 13.7 | 0 | 0 | 0 |
| 4 | α,d-propoxyphene (Darvon) / Flurazepam (Dalmane) | 25 / 50 | 8 | 25.6 | 21.7 | 4 | 4 | 0 |

TABLE I-continued

| Example No. | Compound | Dose (mg/kg) | Number of Mice | Reaction Time at 30 min. after administration | 60 min. after administration | Number with Complete Analgesia at 30 min. after administration | 60 min. after administration | Death |
|---|---|---|---|---|---|---|---|---|
| 5 | α,d-propoxyphene (Darvon) / Flurazepam (Dalmane) | 40 / 50 | 8 | 28.6 | 23.9 | 7 | 3 | 0 |
| Control E1 | Clorazepate (Tranxene) | 50 | 8 | 17.6 | 15.6 | 1 | 1 | 0 |
| 6 | α,d-propoxyphene (Darvon) / Clorazepate (Tranxene) | 25 / 50 | 8 | 27.1 | 24.4 | 5 | 4 | 0 |
| 7 | α,d-propoxyphene (Darvon) / Clorazepate (Tranxene) | 40 / 50 | 8 | 23.6 | 21.8 | 5 | 4 | 0 |
| Control E2 | Clorazepate (Tranxene) | 100 | 8 | 14.4 | 16.5 | 2 | 0 | 0 |
| 8 | α,d-propoxyphene (Darvon) / Clorazepate (Tranxene) | 25 / 100 | 8 | 30.0 | 30.0 | 8 | 8 | 0 |
| 9 | α,d-propoxyphene (Darvon) / Clorazepate (Tranxene) | 40 / 100 | 8 | 29.4 | 26.9 | 7 | 7 | 0 |
| Control F1 | Prazepam | 25 | 8 | 12.3 | 9.5 | 0 | 0 | 0 |
| 10 | Prazepam / α,d-propoxyphene (Darvon) | 25 / 25 | 12 | 23.0 | 20.9 | 7 | 4 | 0 |
| 11 | Prazepam / α,d-propoxyphene (Darvon) | 25 / 40 | 8 | 30 | 25.2 | 8 | 5 | 0 |
| Control F2 | Prazepam | 50 | 8 | 15.9 | 21.3 | 1 | 1 | 0 |
| 12 | Prazepam / α,d-propoxyphene (Darvon) | 50 / 25 | 8 | 25.6 | 28.2 | 3 | 6 | 0 |
| Control G | Lorazepam | 25 | 8 | 11.6 | 13.8 | 0 | 0 | 0 |
| 13 | Lorazepam / α,d-propoxyphene (Darvon) | 25 / 25 | 8 | 25.4 | 12.5 | 5 | 0 | 0 |
| 14 | Lorazepam / α,d-propoxyphene (Darvon) | 25 / 40 | 8 | 29.9 | 20.0 | 6 | 3 | 0 |
| Control H | DDD Azepam | 50 | 8 | 21.9 | 19.3 | 3 | 2 | 0 |
| 15 | DDD Azepam / α,d-propoxyphene (Darvon) | 50 / 25 | 8 | 30.0 | 27.1 | 8 | 6 | 0 |
| Control IA | Compound 3 | 50 | 16 | 10.4 | 9.4 | 0 | 0 | 0 |
| IB | Compound 3 | 100 | 8 | 7.6 | 6.8 | 0 | 0 | 0 |
| IC | Compound 3 and α,d-propoxyphene (Darvon) | 50 / 25 | 8 | 9.1 | 9.9 | 0 | 0 | 0 |
| ID | Compound 3 and α,d-propoxyphene (Darvon) | 50 / 50 | 8 | 11.2 | 11.3 | 0 | 0 | 0 |

Oxazepam (Serax) when tested alone at 25 mg/kg (Control C 1) gave no increase in the reaction time. However, when it was combined with α, d-propoxyphene (Darvon) at 25 mg/kg (Example 1) the reaction time increased to 16.3 seconds for the 30-minute test and 14.5 seconds for the 60-minute test. As is evident, Serax at the 25 mg/kg level is ineffective by itself but with 25 mg/kg of Darvon shows a synergistic effect over Darvon alone at this level (compare with Control B 1).

Oxazepam (Serax) at the 50 mg/kg level when used alone (Control C2) gives a definite increase in the reaction time, both at 30 minutes and at 60 minutes. When combined with 25 mg/kg of α, d-propoxyphene (Darvon) at this level of Oxazepam (Serax) (Example 2), a substantial improvement in the reaction time is noted. However, to achieve best results the α, d-propoxyphene (Darvon) must be increased to 40 mg/kg (Example 3). Twelve of the 16 mice show complete analgesia on the 30-minute test and ten show complete analgesia on the 60-minute test. However, the 40 mg/kg level for α, d-propoxyphene (Darvon) may be considered dangerously high since deaths are observed at the 60 mg/kg level (Control B 3).

Flurazepam (Dalmane) when tested alone at 50 mg/kg (Control D) gave a definite increase in the reaction time to 15.4 and 13.7 seconds. When it was combined with α, d-propoxyphene (Darvon) at 25 mg/kg (Example 4), the reaction time increased to 25.6 seconds for the 30-minute test and 21.7 seconds for the 60-minute test. As is evident, Dalmane with 25 mg/kg of Darvon shows a synergistic effect over Darvon alone at this level (compare with Control B 1). However, to achieve best results the α, d-propoxyphene (Darvon) must be increased to 40 mg/kg (Example 5). Seven of the eight mice show complete analgesia on the 30-minute test, and three show complete analgesia on the 60-minute test.

Clorazepate (Tranxene) at 50 mg/kg (Control E 1) also gave a definite increase in the reaction time, both in the 30-minute and in the 60-minute tests. Further, complete analgesia was obtained with one mouse in both the 30-and the 60-minute tests. Adding 25 mg/kg of Darvon (Example 6) produced a substantially greater increase in the reaction time and complete analgesia in more than half the animals in the 30-minute tests and in half the animals in the 60-minute tests. Increasing the Darvon dosage to 40 mg/kg (Example 7) produced a decrease in the reaction time, though the number of mice showing complete analgesia was unchanged. This decrease may be attributed to experimental error, probably due to variations in the specific reactions of the individual mice.

Increase in the Tranxene level to 100 mg/kg (Control E 2) showed no increase in the reaction time when the Tranxene was used alone. However, when Darvon was added to the extent of 25 mg/kg (Example 8), all of the mice showed complete analgesia. Increase in the Darvon level to 40 mg/kg with Tranxene at 100 mg/kg (Example 9) showed a slight decrease in the reaction time.

Prazepam when tested alone at 25 mg/kg (Control F 1) gave no significant increase in the reaction time. However, when it was combined with $\alpha$, d-propoxyphene (Darvon) at 25 mg/kg (Example 10) the reaction time increased to 23 seconds for the 30-minute test and 20.9 seconds for the 60-minute test. As is evident, Prazepam at the 25 mg/kg level with 25 mg/kg of Darvon shows a synergistic effect over Darvon alone, at this level (compare with Control B).

Prazepam at the 50 mg/kg level when used alone (Control F 2) gives a definite increase in the reaction time both at 30 minutes and at 60 minutes. When combined with 25 mg/kg of $\alpha$, d-propoxyphene (Darvon) at this level (Example 12) a substantial improvement in the reaction time to 25.6 and 28.2 seconds is noted.

However, as Example 11 shows, to achieve best results, the $\alpha$, d-propoxyphene (Darvon) must be increased to 40 mg/kg. All of the eight mice show complete analgesia on the 30-minute test and five show complete analgesia on the 60-minute test.

Lorazepam when tested alone at 25 mg/kg (Control G) gave no significant increase in the reaction time. However, when it was combined with $\alpha$, d-propoxyphene (Darvon) at 25 mg/kg (Example 13), the reaction time increased to 25.4 seconds for the 30-second test but receded to 12.5 seconds for the 60-minute test. As is evident, Lorazepam with 25 mg/kg of Darvon shows a synergistic effect over Darvon alone at this level (compare with Control B 1). However, to achieve best results the $\alpha$, d-propoxyphene (Darvon) must be increased to 40 mg/kg (Example 14). Six out of eight mice show complete analgesia on the 30-minute test, and three show complete analgesia on the 60-minute test.

The results for Example 15 indicate that DDD Azepam markedly increases the analgesic action of $\alpha$, d-propoxyphene. This is of interest because this compound is known to lack tranquilizing or hypnotic properties, and is not medicinally used.

Controls I A, B, C and D show that Compound 3, also pharmaceutically inert, given by itself in doses as high as 100 mg/kg, does not by itself extend the reaction time of mice on the hot plate, nor does it potentiate the analgesic action of $\alpha$, d-propoxyphene (Darvon). This compound is closely related in structure to the benzodiazepines of this invention, but differs from them in not increasing and in not potentiating the analgesic action of $\alpha$, d-propoxyphene.

These results for DDD Azepam and Compound 3 show that the potentiating effect of a benzodiazepine on the analgesic activity of Darvon is not correlated with other pharmacological activity or inactivity. Even benzodiazepines that are not clinically used because they have no tranquilizing, anxiolytic or hypnotic action, can be effective in this invention. Such an inactive compound may, such as DDD Azepam, or may not, such as Compound 3, potentiate the analgesic action of $\alpha$, d-propoxyphene (Darvon). One cannot make predictions from what has been known about the benzodiazepines whether a benzodiazepine will or will not synergistically enhance the analgesic action of $\alpha$, d-propoxyphene (Darvon).

The following are Examples of compositions for dosage units or other application forms in accordance with the invention:

| Tablet formulation | Parts/tablet |
|---|---|
| Active compounds | 15 |
| Lactose | 86 |
| Corn starch (dried) | 45.5 |
| Gelatin | 2.5 |
| Magnesium stearate | 1.0 |

The compound was powdered and passed through a sieve, and well mixed with the lactose and 30 mg of the corn starch.

The mixed powders were combined with a warm gelatin solution prepared by stirring the gelatin in water and heating to form a 10% w/w solution, granulated by passing through a B.S. No. 12 sieve, and the moist granules dried at 40° C.

The dried granules were re-granulated and the balance of the starch and the magnesium stearate were added and thoroughly mixed.

The granules were compressed to produce tablets each weighing 150 mg.

| Tablet formulation | Parts/tablet |
|---|---|
| Active compounds | 100 |
| Lactose | 39 |
| Cornstarch (dried) | 80 |
| Gelatin | 4.0 |
| Magnesium stearate | 2.0 |

The method of preparation is identical with that of the preceeding, except that 60 parts of starch is used in the granulation process and 20 parts during tableting.

| Capsule formulation | Parts/capsule |
|---|---|
| Active compounds | 250 |
| Lactose | 150 |

The compounds and lactose were passed through a sieve and the powders well mixed together before filling into hard gelatin capsules of suitable size, so that each capsule contained 400 mg.

| Suppositories | Parts/suppository |
|---|---|
| Active compounds | 50 |
| Cocoa butter | 950 |

The compounds were powdered and passed through a sieve and triturated with molten cocoa butter at 45° C to form a smooth suspension.

The mixture was well stirred and poured into moulds, each of nominal 1 g capacity, to produce suppositories.

| Cachets | |
|---|---|
| | Parts/cachet |
| Active compounds | 100 |
| Lactose | 400 |

The compounds were passed through a sieve, mixed with lactose previously sieved and filled into cachets of suitable size so that each contained 500 mg.

| Intramuscular injection (suspension in aqueous vehicle) | |
|---|---|
| | Parts |
| Compounds | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml. | |

The sodium citrate and sodium carboxymethylcellulose were mixed with sufficient water for injection at 90° C. The mixture was cooled to 50° C and the methyl and propyl para-hydroxybenzoates added followed by the medicament previously milled and sieved 300 mesh. When cooled the injection was made up to volume and sterilized by heating in an autoclave.

Having regard to the foregoing disclosure, the following is claimed as the inventive and patentable embodiments thereof:

1. An analgesic composition having a remarkably high analgesic activity, comprising as analgesically active components, α, d-propoxyphene or pharmaceutically acceptable salt thereof and at least one benzodiazepine or pharmaceutically acceptable salt thereof, in an amount within the weight ratio range of α, d-propoxyphene:benzodiazepine from 100:0.5 to 2:1, the benzodiazepine enhancing the analgesic activity of the α, d-propoxyphene when administered separately, the benzodiazepine having the formula:

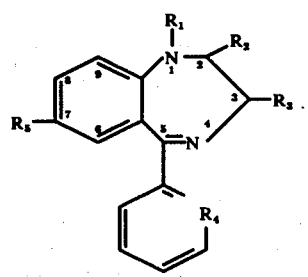

wherein:

$R_1$ is selected from the group consisting of hydrogen, n-butyl, and alkylamino

where R and R' are selected from the group consisting of hydrogen, lower alkyl having from one to three carbon atoms, and bivalent alkylene having from two to four carbon atoms and linked to the nitrogen at two positions to form a heterocyclic ring;

$R_2$ is selected from the group consisting of oxo oxygen = O and hydroxyl OH;

$R_3$ is selected from the group consisting of hydrogen, hydroxyl OH and carboxyl COOH;

$R_4$ is selected from the group consisting of

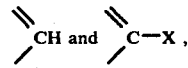

where X is Cl or F; and $R_5$ is selected from the group consisting of hydrogen, Cl and F.

2. An analgesic composition in accordance with claim 1 in which the benzodiazepine is selected from the group consisting of oxazepam, clorazepate, flurazepam, lorazepam, prazepam, and DDD azepam.

3. An analgesic composition in accordance with claim 1 in which $R_1$ is hydrogen.

4. An analgesic composition in accordance with claim 1 in which $R_1$ is $(CH_2)_2CH_3$.

5. An analgesic composition in accordance with claim 1 in which $R_1$ is

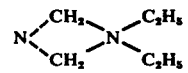

6. An analgesic composition in accordance with claim 1 in which $R_2$ is = O.

7. An analgesic composition in accordance with claim 1 in which $R_2$ is OH.

8. An analgesic composition in accordance with claim 1 in which $R_3$ is OH.

9. An analgesic composition in accordance with claim 2 in which $R_3$ is COOH.

10. An analgesic composition in accordance with claim 1 in which $R_3$ is hydrogen.

11. An analgesic composition in accordance with claim 1 in which $R_4$ is

12. An analgesic composition in accordance with claim 1 in which $R_4$ is

13. An analgesic composition in accordance with claim 1 in which $R_4$ is

14. An analgesic composition in accordance with claim 1 in which $R_5$ is Cl.

15. An analgesic composition in accordance with claim 1 in which $R_5$ is H.

16. A process for obtaining an analgesic effect, which comprises administering α, d-propoxyphene or pharmaceutically acceptable salt thereof and at least one benzodiazepine or pharmaceutically acceptable salt thereof, in an amount within the weight ratio range of α, d-propoxyphene: benzodiazepine from 100:0.5 to 2:1, the benzodiazepine enhancing the analgesic activity of the α, d-propoxyphene when administered separately, the benzodiazepine having the formula:

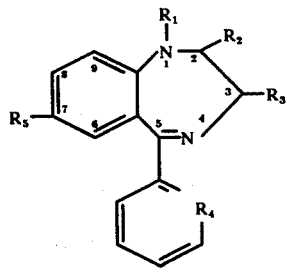

wherein:
$R_1$ is selected from the group consisting of hydrogen, n-butyl, and alkylamino

where R and R' are selected from the group consisting of hydrogen, lower alkyl having from one to three carbon atoms, and bivalent alkylene having from two to four carbon atoms and linked to the nitrogen at two positions to form a heterocyclic ring;

$R_2$ is selected from the group consisting of oxo oxygen = O and hydroxyl OH;

$R_3$ is selected from the group consisting of hydrogen, hydroxyl OH and carboxyl COOH;

$R_4$ is selected from the group consisting of CH and C—X, where X is Cl or F; and $R_5$ is selected from the group consisting of hydrogen, Cl and F.

17. A process in accordance with claim 16 in which the benzodiazepine is selected from the group consisting of oxazepam, clorazepate, flurazepam, lorazepam, prazepam, and DDD azepam.

18. A pharmaceutical composition in dosage unit form comprising an analgesic composition in accordance with claim 1 and a pharmaceutically acceptable carrier, the unit dose comprising from about 25 to about 200 mg of the α, d-propoxyphene calculated as the free base and from about 0.5 to about 25 mg of the benzodiazepine calculated as the free base.

* * * * *

UNITED STATES PATENT OFFICE
CERTIFICATE OF CORRECTION

Patent No. 4,028,466          Dated June 7, 1977

Inventor(s) Frank M. Berger

It is certified that error appears in the above-identified patent and that said Letters Patent are hereby corrected as shown below:

On the cover sheet under (*) Notice, "April 12, 1994"

should read -- June 7, 1994 --.

*Signed and Sealed this*

*Sixth* Day of *September 1977*

[SEAL]

Attest:

RUTH C. MASON          LUTRELLE F. PARKER
*Attesting Officer*         *Acting Commissioner of Patents and Trademarks*